(12) United States Patent
Okayama et al.

(10) Patent No.: US 11,980,691 B2
(45) Date of Patent: May 14, 2024

(54) ENTERIC SOFTGEL CAPSULES

(71) Applicant: R.P. SCHERER TECHNOLOGIES, LLC, Las Vegas, NV (US)

(72) Inventors: Toshikazu Okayama, Shizuoka Pref. (JP); Miyako Takahashi, Shizuoka Pref. (JP); Takuma Fujii, Shizuoka Pref. (JP)

(73) Assignee: R.P. Scherer Technologies, LLC, Las Vegas, NV (US)

(*) Notice: Subject to any disclaimer, the term of this patent is extended or adjusted under 35 U.S.C. 154(b) by 0 days.

(21) Appl. No.: 16/979,485

(22) PCT Filed: Mar. 15, 2019

(86) PCT No.: PCT/US2019/022411
§ 371 (c)(1),
(2) Date: Sep. 9, 2020

(87) PCT Pub. No.: WO2019/178444
PCT Pub. Date: Sep. 19, 2019

(65) Prior Publication Data
US 2021/0038526 A1 Feb. 11, 2021

Related U.S. Application Data

(60) Provisional application No. 62/643,521, filed on Mar. 15, 2018.

(51) Int. Cl.
*A61K 9/48* (2006.01)

(52) U.S. Cl.
CPC .......... *A61K 9/4825* (2013.01); *A61K 9/4816* (2013.01); *A61K 9/4833* (2013.01)

(58) Field of Classification Search
CPC ... A61K 9/4825; A61K 9/4816; A61K 9/4833
See application file for complete search history.

(56) References Cited

U.S. PATENT DOCUMENTS

| | | |
|---|---|---|
| 6,410,050 B1 | 6/2002 | Yang |
| 7,041,315 B2 | 5/2006 | Scott et al. |
| 7,220,434 B2 | 5/2007 | Desai et al. |
| 7,498,309 B2 | 3/2009 | Levy |
| 8,309,107 B2 | 11/2012 | Liu et al. |
| 9,011,908 B2 | 4/2015 | Liu et al. |
| 9,056,058 B2 * | 6/2015 | Yulai .......... A61P 9/12 |
| 9,056,122 B2 | 6/2015 | Asada et al. |
| 9,180,104 B2 | 11/2015 | Nelson et al. |
| 9,370,493 B2 | 6/2016 | Berge et al. |
| 9,408,823 B2 | 8/2016 | Nelson et al. |
| 9,504,656 B2 | 11/2016 | Vamvakas et al. |
| 10,182,989 B2 | 1/2019 | Fang et al. |
| 10,182,991 B2 | 1/2019 | Dyakonov et al. |
| 10,463,625 B2 | 11/2019 | Cade et al. |
| 2003/0175335 A1 * | 9/2003 | Scott .......... A61Q 19/00 424/452 |
| 2005/0158377 A1 * | 7/2005 | Popp .......... A61K 9/4866 424/451 |
| 2006/0165778 A1 | 7/2006 | Hassan et al. |
| 2010/0062057 A1 | 3/2010 | Berge et al. |
| 2010/0173002 A1 * | 7/2010 | Yulai .......... A61P 3/02 424/490 |
| 2012/0141531 A1 * | 6/2012 | Coulter .......... A61K 9/1694 424/236.1 |
| 2012/0196936 A1 | 8/2012 | Kim et al. |
| 2012/0301546 A1 | 11/2012 | Hassan |
| 2012/0315332 A1 | 12/2012 | Ling et al. |
| 2013/0108696 A1 | 5/2013 | Berge et al. |
| 2013/0115285 A1 | 5/2013 | Van Ness et al. |
| 2013/0251792 A1 | 9/2013 | Kowalski et al. |
| 2013/0259933 A1 | 10/2013 | Kamaguchi et al. |
| 2013/0280323 A1 | 10/2013 | Fang et al. |
| 2014/0343027 A1 | 11/2014 | Rogawski |
| 2015/0132374 A1 | 5/2015 | Coulter et al. |
| 2015/0132396 A1 * | 5/2015 | Coulter .......... A61K 9/0053 514/567 |
| 2015/0299433 A1 | 10/2015 | Shuai et al. |
| 2015/0335586 A1 | 11/2015 | Baruzzi et al. |
| 2015/0342893 A1 * | 12/2015 | Coulter .......... A61K 31/635 424/490 |
| 2016/0000740 A1 | 1/2016 | Zhang et al. |
| 2016/0143989 A1 | 5/2016 | Coulter et al. |
| 2016/0279056 A1 | 9/2016 | Zhao et al. |
| 2016/0324919 A1 | 11/2016 | Coulter |

FOREIGN PATENT DOCUMENTS

| | | |
|---|---|---|
| EP | 3205339 A1 | 8/2017 |
| JP | H11-76369 A | 3/1999 |
| JP | 2004217566 A | 8/2004 |

(Continued)

OTHER PUBLICATIONS

Al-Tabakha, Moawia M., "HPMC Capsules: Current Status and Future Prospects", J. Pharm Pharmaceutical Science, 13 (3), 428-442, 2010.
Sahar Abd El-Sattar Fahmy, J. Mark Christensen & James W. Ayres (2009) Development of novel spray coated soft elastic gelatin capsule sustained release formulations of nifedipine, Drug Development and Industrial Pharmacy, 35:8, 1009-1021; https://doi.org/10.1080/03639040902725182.
Abdul W. Basit, "Advances in Colonic Drug Delivery", The School of Pharmacy, University of London, Drugs 2005, 65 (14), 1991-2007.

(Continued)

*Primary Examiner* — Shirley V Gembeh
*Assistant Examiner* — Olga V. Tcherkasskaya
(74) *Attorney, Agent, or Firm* — Lowenstein Sandler LLP

(57) ABSTRACT

Enteric softgel capsules comprise a fill material and an enteric shell composition, characterized in that the enteric nature of the capsules may be achieved without an enteric coating or added conventional enteric polymers.

19 Claims, No Drawings

(56) References Cited

FOREIGN PATENT DOCUMENTS

| | | |
|---|---|---|
| JP | 2005-025609 A | 1/2005 |
| JP | 2006-505542 A | 2/2006 |
| JP | 2006-082824 A | 3/2006 |
| JP | 2007-161694 A | 6/2007 |
| JP | 2007518808 A | 7/2007 |
| JP | 2008-024696 A | 2/2008 |
| JP | 2009-116382 A | 5/2009 |
| JP | 2009-185022 A | 8/2009 |
| JP | 2011-148703 A | 8/2011 |
| JP | 201047548 A | 9/2011 |
| JP | 2012-510438 A | 5/2012 |
| JP | 2013-505292 A | 2/2013 |
| JP | 2013-508348 A | 3/2013 |
| JP | 2013-095750 A | 5/2013 |
| JP | 2013-515680 A | 5/2013 |
| JP | 2013-519686 A | 5/2013 |
| JP | 2013-226095 A | 11/2013 |
| JP | 2014-015431 A | 1/2014 |
| JP | 2015-512945 A | 4/2015 |
| JP | 2015-515962 A | 6/2015 |
| JP | 2015-189684 A | 11/2015 |
| JP | 2016-014027 A | 1/2016 |
| JP | 2016-513674 A | 5/2016 |
| JP | 2016-517422 A | 6/2016 |
| KR | 101607459 B1 | 3/2016 |
| WO | 2003080026 A1 | 10/2003 |
| WO | 2005/025609 A1 | 3/2005 |
| WO | 2005072686 A1 | 8/2005 |
| WO | 2006115712 A2 | 11/2006 |
| WO | 2007044488 A1 | 4/2007 |
| WO | 2010/060667 A1 | 6/2010 |
| WO | 2011060944 A2 | 5/2011 |
| WO | 2012013331 A2 | 2/2012 |
| WO | 2013153451 A2 | 10/2013 |
| WO | 2014028398 A2 | 2/2014 |
| WO | 2014031213 A1 | 2/2014 |
| WO | 2015035513 A1 | 3/2015 |
| WO | 2015195989 A1 | 12/2015 |
| WO | 2015200149 A1 | 12/2015 |
| WO | 2016044805 A1 | 3/2016 |
| WO | 2016056230 A1 | 4/2016 |
| WO | 2016140933 A2 | 9/2016 |

OTHER PUBLICATIONS

Kanabar et al. "DUOCAP: The Capsule in Capsule Technology", International Research Journal of Pharmacy, 2015, 6 (2), ISSN 2230-8407, 4 pages.

International Search Report and Written Opinion for International Patent Application No. PCT/US19/22411 dated Jun. 3, 2019, 38 pages.

Gullapalli Rampurna et al., "Gelatin and 1-15 Non-Gelatin Capsul Dosage Forms", Journal of Phararmaceutical Sciences, Elsevier Inc., US, vol. 106, No. 6, May 31, 2017, 8 pages.

Extend European Search Report for Application No. 19768554.8 dated Jan. 27, 2022, 8 pages.

\* cited by examiner

ENTERIC SOFTGEL CAPSULES

CROSS-REFERENCE TO RELATED APPLICATION(S)

This application is a national phase of International Application No. PCT/US2019/022411, filed on Mar. 15, 2019, which claims the benefit of U.S. Provisional Patent Application No. 62/643,521, filed on Mar. 15, 2018. The contents of these applications are hereby incorporated by reference in their entirety.

FIELD OF THE INVENTION

The present invention relates to enteric softgel capsules, wherein the gelatin-based shell compositions possess enteric properties without the need for enteric coatings or the addition of conventional enteric polymers.

BACKGROUND OF THE INVENTION

Soft capsules, in particular, soft gelatin capsules (or softgel capsules), provide a dosage form which is more readily accepted by patients, since the capsules are easy to swallow and need not be flavored in order to mask any unpleasant taste of the active agent. Softgel encapsulation of drugs further provides the potential to improve the bioavailability of the pharmaceutical agents. For example, active ingredients may be rapidly released in liquid form as soon as the gelatin shell ruptures.

Efforts have been made to create enteric dosage forms. Enteric dosage forms are designed to protect the contents of the dosage form from gastric conditions. For example, enteric dosage forms may be produced by adding an enteric coating to the surface of a manufactured dosage form such as a tablet or a capsule. Such coatings may be applied through spraying the dosage form, followed by drying the dosage form, usually at elevated temperatures. This method of coating a capsule with an enteric coating may lead to disadvantages in terms of performance and appearance. For example, the capsule may appear rough, the coating may be applied unevenly, and/or the coating can be prone to cracking or flaking off the dosage form. Additionally, the process of applying an enteric coating is very inefficient.

Other enteric dosage forms have been developed in which conventional enteric polymers (i.e., acid-insoluble polymers) are added in the capsule shell. However, the addition of conventional enteric polymers can lead to capsules that are prone to leaking due to insufficient sealing.

Accordingly, there is currently a need for an enteric softgel capsule that does not require either an application of an enteric coating or the addition of conventional enteric polymers in the shell.

Surprisingly, it was found that the gelatin-based shell compositions of the present invention possessed satisfactory enteric properties without the need to apply an enteric coating or incorporate a conventional enteric polymer.

SUMMARY OF THE INVENTION

The present invention is directed to enteric softgel capsules. The enteric softgel capsules comprise (a) a fill material and (2) an enteric shell composition. The enteric softgel capsules according to the present invention do not include either an enteric coating or an added conventional enteric polymer. Accordingly, the enteric shell composition eliminates the need to add an enteric coating, which also minimizes the risk of damaging the capsules during the coating process.

In an embodiment, the enteric shell composition comprises: (a) a gelatin, (b) a cellulose derivative such as hydroxypropyl methyl cellulose ("HPMC"), (c) a pectin such as a low methoxy pectin and (d) a plasticizer. The present invention is also directed to a process of making enteric softgel capsules.

DETAILED DESCRIPTION OF THE INVENTION

The present invention advances the state of the art by developing enteric oral dosage forms, in particular, enteric softgel capsules, that achieves the advantages associated with the conventional enteric dosage forms without the need to apply an enteric coating or to add conventional enteric polymer in the capsule shell. The enteric softgel capsules of the present invention do not dissolve in a gastric environment of the stomach, but rather dissolve in the intestines. Such mechanism is beneficial for delivery of active ingredients that may cause stomach irritation or are sensitive to the acidic environment of the stomach.

As used herein, the term "enteric" is used to refer to the dissolution or disintegration resistant property of a substance such that dissolution or disintegration does not occur in a gastric environment. For example, the embodiments described herein include an enteric shell composition that dissolves in biological, artificial or simulated intestinal fluid rather than in biological, artificial or simulated gastric fluid. As used herein, "pharmaceutically active ingredient" refers to a drug or compound that may be used in the diagnosis, cure, mitigation, treatment, or prevention of a condition. The term "condition" or "conditions" refers to those medical conditions that can be treated or prevented by administration to a subject of an effective amount of an active agent. Exemplary non-limiting conditions that may benefit from enteric softgel capsules may include, without limitations, capsules containing lactic acid bacteria, fish oil capsules, proton pump inhibitors, aspirin and similar products.

As used herein, the term "active ingredient" refers to any material that is intended to produce a therapeutic, prophylactic, or other intended effect, whether or not approved by a government agency for that purpose. This term with respect to a specific agent includes the pharmaceutically active agent, and all pharmaceutically acceptable salts, solvates and crystalline forms thereof, where the salts, solvates and crystalline forms are pharmaceutically active.

Any pharmaceutically active ingredient may be used for purposes of the present invention, including both those that are water-soluble and those that are poorly soluble in water. Suitable pharmaceutically active ingredients include, without limitation, analgesics and anti-inflammatory agents, antacids, anthelmintic, anti-arrhythmic agents, anti-bacterial agents, anti-coagulants, anti-depressants, anti-diabetics, anti-diarrheal, anti-epileptics, anti-fungal agents, anti-gout agents, anti-hypertensive agents, anti-malarial, anti-migraine agents, anti-muscarinic agents, anti-neoplastic agents and immunosuppressants, anti-protozoal agents, anti-rheumatics, anti-thyroid agents, antivirals, anxiolytics, sedatives, hypnotics and neuroleptics, beta-blockers, cardiac inotropic agents, corticosteroids, cough suppressants, cytotoxics, decongestants, diuretics, enzymes, anti-parkinsonian agents, gastro-intestinal agents, histamine receptor antagonists, lipid regulating agents, local anesthetics, neuromuscular agents, nitrates and anti-anginal agents, nutritional agents, opioid analgesics, oral vaccines, proteins, peptides and recombinant drugs, sex hormones and contraceptives, spermicides, stimulants, and combinations thereof.

In some embodiments, the active pharmaceutical ingredient may be selected, without limitations, from the group consisting of dabigatran, dronedarone, ticagrelor, iloperidone, ivacaftor, midostaurine, asimadoline, beclomethasone, apremilast, sapacitabine, linsitinib, abiraterone, vitamin D analogs (e.g., calcifediol, calcitriol, paricalcitol, doxercalciferol), COX-2 inhibitors (e.g., celecoxib, valdecoxib, rofecoxib), tacrolimus, testosterone, lubiprostone, pharmaceutically acceptable salts thereof, and combinations thereof.

In some embodiments, the lipids in the dosage form may be selected, without limitations, from the group consisting of, almond oil, argan oil, avocado oil, borage seed oil, canola oil, cashew oil, castor oil, hydrogenated castor oil, cocoa butter, coconut oil, colza oil, corn oil, cottonseed oil, grape seed oil, hazelnut oil, hemp oil, hydroxylated lecithin, lecithin, linseed oil, macadamia oil, mango butter, manila oil, mongongo nut oil, olive oil, palm kernel oil, palm oil, peanut oil, pecan oil, perilla oil, pine nut oil, pistachio oil, poppy seed oil, pumpkin seed oil, rice bran oil, safflower oil, sesame oil, shea butter, soybean oil, sunflower oil, hydrogenated vegetable oil, walnut oil, and watermelon seed oil. Other oil and fats may include, but not be limited to, fish oil (omega-3), krill oil, animal or vegetable fats, e.g., in their hydrogenated form, free fatty acids and mono-, di-, and tri-glycerides with C8-, C10-, C12-, C14-, C16-, C18-, C20- and C22-fatty acids, and combinations thereof.

According to certain embodiments, active agents may include lipid-lowering agents including, but not limited to, statins (e.g., lovastatin, simvastatin, pravastatin, fluvastatin, atorvastatin, rosuvastatin, and pitavastatin), fibrates (e, g, clofibrate, ciprofibrate, bezafibrate, fenofibrate, and gemfibrozil), niacin, bile acid sequestrants, ezetimibe, lomitapide, phytosterols, and the pharmaceutically acceptable salts, hydrates, solvates and prodrugs thereof, mixtures of any of the foregoing, and the like.

Suitable nutraceutical active agents may include, but are not limited to, 5-hydroxytryptophan, acetyl L-carnitine, alpha lipoic acid, alpha-ketoglutarates, bee products, betaine hydrochloride, bovine cartilage, caffeine, cetyl myristoleate, charcoal, chitosan, choline, chondroitin sulfate, coenzyme Q10, collagen, colostrum, creatine, cyanocobalamin (Vitamin 812), dimethylaminoethanol, fumaric acid, germanium sequioxide, glandular products, glucosamine HCI, glucosamine sulfate, hydroxyl methyl butyrate, immunoglobulin, lactic acid, L-Carnitine, liver products, malic acid, maltose-anhydrous, mannose (d-mannose), methyl sulfonyl methane, phytosterols, picolinic acid, pyruvate, red yeast extract, S-adenosylmethionine, selenium yeast, shark cartilage, theobromine, vanadyl sulfate, and yeast.

Suitable nutritional supplement active agents may include vitamins, minerals, fiber, fatty acids, amino acids, herbal supplements or a combination thereof.

Suitable vitamin active agents may include, but are not limited to, the following: ascorbic acid (Vitamin C), B vitamins, biotin, fat soluble vitamins, folic acid, hydroxycitric acid, inositol, mineral ascorbates, mixed tocopherols, niacin (Vitamin B3), orotic acid, para-aminobenzoic acid, panthothenates, panthothenic acid (Vitamin B5), pyridoxine hydrochloride (Vitamin B6), riboflavin (Vitamin B2), synthetic vitamins, thiamine (Vitamin B1), tocotrienols, vitamin A, vitamin D, vitamin E, vitamin F, vitamin K, vitamin oils and oil soluble vitamins.

Suitable herbal supplement active agents may include, but are not limited to, the following: arnica, bilberry, black cohosh, cat's claw, chamomile, echinacea, evening primrose oil, fenugreek, flaxseed, feverfew, garlic, ginger root, ginko biloba, ginseng, goldenrod, hawthorn, kava-kava, licorice, milk thistle, psyllium, rauowolfia, senna, soybean, St. John's wort, saw palmetto, turmeric, valerian.

Minerals active agents may include, but are not limited to, the following: boron, calcium, chelated minerals, chloride, chromium, coated minerals, cobalt, copper, dolomite, iodine, iron, magnesium, manganese, mineral premixes, mineral products, molybdenum, phosphorus, potassium, selenium, sodium, vanadium, malic acid, pyruvate, zinc and other minerals.

Examples of other possible active agents include, but are not limited to, antihistamines (e.g., ranitidine, dimenhydrinate, diphenhydramine, chlorpheniramine and dexchlorpheniramine maleate), non-steroidal anti-inflammatory agents (e.g., aspirin, celecoxib, Cox-2 inhibitors, diclofenac, benoxaprofen, flurbiprofen, fenoprofen, flubufen, indoprofen, piroprofen, carprofen, oxaprozin, pramoprofen, muroprofen, trioxaprofen, suprofen, aminoprofen, fluprofen, bucloxic acid, indomethacin, sulindac, zomepirac, tiopinac, zidometacin, acemetacin, fentiazac, clidanac, oxpinac, meclofenamic acid, flufenamic acid, niflumic acid, tolfenamic acid, diflurisal, flufenisal, piroxicam, sudoxicam, isoxicam, aceclofenac, aloxiprin, azapropazone, benorilate, bromfenac, carprofen, choline magnesium salicylate, diflunisal, etodolac, etoricoxib, faislamine, fenbufen, fenoprofen, flurbiprofen, ibuprofen, indometacin, ketoprofen, ketorolac, lomoxicam, loxoprofen, meloxicam, mefenamic acid, metamizole, methyl salicylate, magnesium salicylate, nabumetone, naproxen, nimesulide, oxyphenbutazone, parecoxib, phenylbutazone, salicyl salicylate, sulindac, sulfinpyrazone, tenoxicam, tiaprofenic acid, tolmetin. pharmaceutically acceptable salts thereof and mixtures thereof) and acetaminophen, anti-emetics (e.g., metoclopramide, methylnaltrexone), anti-epileptics (e.g., phenyloin, meprobmate and nitrazepam), vasodilators (e.g., nifedipine, papaverine, diltiazem and nicardipine), anti-tussive agents and expectorants (e.g. codeine phosphate), anti-asthmatics (e.g. theophylline), antacids, anti-spasmodics (e.g. atropine, scopolamine), antidiabetics (e.g., insulin), diuretics (e.g., ethacrynic acid, bendrofluthiazide), anti-hypotensives (e.g., propranolol, clonidine), antihypertensives (e.g., clonidine, methyldopa), bronchodilatiors (e.g., albuterol), steroids (e.g., hydrocortisone, triamcinolone, prednisone), antibiotics (e.g., tetracycline), antihemorrhoidals, hypnotics, psychotropics, antidiarrheals, mucolytics, sedatives, decongestants (e.g. pseudoephedrine), laxatives, vitamins, stimulants (including appetite suppressants such as phenylpropanolamine) and cannabinoids, as well as pharmaceutically acceptable salts, hydrates, solvates, and prodrugs thereof.

The active agent that may also be a benzodiazepine, barbiturate, stimulants, or mixtures thereof. The term "benzodiazepines" refers to a benzodiazepine and drugs that are derivatives of a benzodiazepine that are able to depress the central nervous system. Benzodiazepines include, but are not limited to, alprazolam, bromazepam, chlordiazepoxide, clorazepate, diazepam, estazolam, flurazepam, halazepam, ketazolam, lorazepam, nitrazepam, oxazepam, prazepam, quazepam, temazepam, triazolam, methylphenidate as well as pharmaceutically acceptable salts, hydrates, solvates, prodrugs and mixtures thereof. Benzodiazepine antagonists that can be used as active agent include, but are not limited to, flumazenil as well as pharmaceutically acceptable salts, hydrates, solvates and mixtures thereof.

The term "barbiturates" refers to sedative-hypnotic drugs derived from barbituric acid (2, 4, 6,-trioxohexahydropyrimidine). Barbiturates include, but are not limited to, amobarbital, aprobarbotal, butabarbital, butalbital, methohexital, mephobarbital, metharbital, pentobarbital, phenobarbital, secobarbital as well as pharmaceutically acceptable salts, hydrates, solvates, prodrugs, and mixtures thereof. Barbiturate antagonists that can be used as active agent include, but are not limited to, amphetamines as well as pharmaceutically acceptable salts, hydrates, solvates and mixtures thereof.

The term "stimulants" includes, but is not limited to, amphetamines such as dextroamphetamine resin complex, dextroamphetamine, methamphetamine, methylphenidate, as well as pharmaceutically acceptable salts, hydrates, and solvates and mixtures thereof. Stimulant antagonists that can be used as active agent include, but are not limited to, benzodiazepines, as well as pharmaceutically acceptable salts, hydrates, solvates and mixtures thereof.

The dosage forms according to the disclosure include various active agents and their pharmaceutically acceptable salts thereof. Pharmaceutically acceptable salts include, but are not limited to, inorganic acid salts such as hydrochloride, hydrobromide, sulfate, phosphate and the like; organic acid salts such as formate, acetate, trifluoroacetate, maleate, tartrate and the like; sulfonates such as methanesulfonate, benzenesulfonate, p-toluenesulfonate, and the like; amino acid salts such as arginate, asparginate, glutamate and the like, and metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like.

As used herein, the terms "therapeutically effective" and an "effective amount" refer to the amount of active agent or the rate at which it is administered which is needed to produce a desired therapeutic result.

As used herein, "shell" or "shell composition" refers to the shell of a softgel capsule which encapsulates a fill material.

As used herein, "conventional enteric polymers" refer to, but are not limited to, acrylic and methacrylic acid polymers, which may be available under the tradename EUDRAGIT® and other conventional acid insoluble polymers, e.g., methyl acrylate-methacrylic acid copolymers. Other conventional acid insoluble polymers include, without limitation, cellulose acetate succinate, cellulose acetate phthalate, cellulose acetate butyrate, hydroxypropyl methyl cellulose phthalate, hydroxy propyl methyl cellulose acetate succinate (hypermellose acetate succinate), polyvinyl acetate phthalate (PVAP), algenic acid salts such as sodium alginate and potassium alginate, stearic acid, and shellac. In some embodiments, the enteric shell composition of the present invention does not include an acid insoluble polymer. In other words, the enteric shell composition and the enteric softgel capsule are "free or substantially free of conventional enteric polymers."

As used herein, "free or substantially free," refers to a composition that comprises less than about 1 wt %, less than about 0.5 wt %, less than about 0.25 wt %, less than about 0.1 wt %, less than about 0.05 wt %, less than about 0.01 wt %, or 0 wt % of said component.

All references to wt % throughout the specifications and the claims refer to the weight of the component in reference to the weight of the entire composition and may also be designated as w/w.

As used herein, "fill material" or "fill" refers to the composition that is encapsulated by the enteric capsule shell and contains at least one pharmaceutically active ingredient.

As used herein, "enteric capsules" or "enteric softgel capsules" refer to capsules which have enteric properties once the fill material is encapsulated in the shell, and the capsules are dried. No further processing steps are required.

As used herein, "about" refers to any values that are within a variation of ±10%, such that "about 10" would include from 9 to 11. As used herein, "a," "an," or "the" refers to one or more, unless otherwise specified. Thus, for example, reference to "an excipient" includes a single excipient as well as a mixture of two or more different excipients, and the like.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

The use of any and all examples, or exemplary language (e.g., "such as") provided herein, is intended merely to illuminate certain materials and methods and does not pose a limitation on scope. No language in the specification should be construed as indicating any non-claimed element as essential to the practice of the disclosed materials and methods.

According to a first embodiment, an enteric softgel capsule comprises (a) a fill material and (b) an enteric shell composition, wherein the fill material comprises at least one pharmaceutically active ingredient, wherein the enteric shell composition comprises a gelatin, a cellulose derivative such as hydroxypropyl methyl cellulose (HPMC), a low methoxy pectin and a plasticizer, and wherein the enteric shell composition is free of conventional enteric polymers.

Suitable fill materials comprise at least one pharmaceutically active ingredient and can be made according to known methods. In addition to the at least one pharmaceutically active ingredient, suitable fill materials may comprise additional fill components such as flavoring agents, sweetening agents, coloring agents and fillers or other pharmaceutically acceptable excipients or additives such as synthetic dyes and mineral oxides. Suitable amounts of pharmaceutically active ingredient and pharmaceutically acceptable excipients can be readily determined by one of ordinary skill in the art.

In an embodiment, the gelatin in the enteric shell composition may include Type A gelatin, Type B gelatin, a hide gelatin and/or a bone gelatin used alone or in combination. In one embodiment, the gelatin is a 250 bloom gelatin. In another embodiment, there is only one type of gelatin. In yet another embodiment, the gelatin is a combination of at least two types of gelatins. In an embodiment, the amount of gelatin in the enteric shell composition is about 40 wt % to about 80 wt %, more preferably from about 45 wt % to about 75 wt %, and most preferably from about 50 wt % to about 70 wt %.

In one embodiment, the enteric capsule shell composition comprises HPMC. In an embodiment, the amount of cellulose derivative (e.g., HPMC) in the enteric capsule shell composition is about 0.15 wt % to about 4.0 wt %, more preferably from about 0.20 wt % to about 2.0 wt %, and most preferably from about 0.25 wt % to about 1.4 wt %. In some embodiments, the enteric capsule shell composition may comprise HPMC, methyl cellulose (MC), hydroxypropyl-cellulose (HPC), or combinations thereof. The cellulose derivative may be added to the enteric capsule shell to mitigate potential reduction in gel strength. The concentration of cellulose derivative in the enteric shell composition may be in an effective amount to improve the gel strength but not so high that it would interfere with the seal.

In some embodiments, the enteric shell composition may comprise pectin, e.g., a low methoxy pectin. In an embodiment, the low methoxy pectin may be LM Pectin (P-25), LM Pectin (445C), LM Pectin (100C) or a combination thereof. The addition of pectin contributes to the enteric nature of the dosage form. However, too much pectin in the dosage form may reduce the gel strength of the softgel capsule which may in turn adversely affect the sealability of the softgel capsule. Therefore, pectin may be added to the dosage form at a concentration that is sufficiently high to form an enteric dosage form and at the same time is sufficiently low to mitigate the reduction in gel strength. In an embodiment, an amount of low methoxy pectin in the enteric shell composition is about 2 wt % to about 20 wt %, from about 3 wt % to about 15 wt %, from about 3 wt % to about 5.5 wt %, and from about 5 wt % to about 10 wt %. The degree of esterification of the pectin incorporated in the enteric shell composition may be lower than about 50%, or may range from about 10% to about 50%, from about 20% to about 40%, or from about 25% to about 35%. In an embodiment, the plasticizer in the enteric shell composition may include glycerol, glycerin, sorbitol and combinations thereof. Other suitable plasticizers may include, but not be limited to, sugar alcohol plasticizer such as isomalt, maltitol, xylitol, erythritol, adonitol, dulcitol, pentaerythritol, or mannitol; or polyol plasticizer such as diglycerin, ethylene glycol, diethylene glycol, triethyleneglycol, tetraethylene glycol, dipropylene glycol, a polyethylene glycol up to 10,000 MW, neopentyl glycol, propylene glycol, 1,3-propanediol, 2-methyl-1,3-propanediol, trimethylolpropane, a polyether polyol, ethanol amines; and mixtures thereof. Other exemplary plasticizers may also include, without limitations, low molecular weight polymers, oligomers, copolymers, oils, small organic molecules, low molecular weight polyols having aliphatic hydroxyls, ester-type plasticizers, glycol ethers, poly(propylene glycol), multi-block polymers, single block polymers, citrate ester-type plasticizers, and triacetin. Such plasticizers may include 1,2-butylene glycol, 2,3-butylene glycol, styrene glycol, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutyl sebacate, acetyltributylcitrate, triethyl citrate, glyceryl monostearate, polysorbate 80, acetyl triethyl citrate, tributyl citrate and allyl glycolate, and mixtures thereof.

In an embodiment, the amount of plasticizer in the enteric shell composition is about 15 wt % to about 40 wt %, more preferably from about 20 wt % to about 35 wt %, and most preferably from about 25 wt % to about 30 wt %.

In an embodiment, the enteric shell composition and the enteric softgel capsule capsule may be free or substantially free of conventional enteric polymers.

In an embodiment, the enteric shell composition and the enteric softgel capsule may be free or substantially free of divalent cation salts, such as $Ca^{++}$ (e.g., $CaCl_2$) or $Mg^{++}$ (e.g., $MgCl_2$).

In an embodiment, the enteric shell composition may optionally comprise additional agents such as coloring agents, flavorings agents, sweetening agents, fillers, antioxidants, diluents, pH modifiers or other pharmaceutically acceptable excipients or additives such as synthetic dyes and mineral oxides.

Exemplary suitable coloring agents may include, but not be limited to, colors such as e.g., white, black, yellow, blue, green, pink, red, orange, violet, indigo, and brown. In specific embodiments, the color of the dosage form can indicate the contents (e.g., one or more active ingredients) contained therein.

Exemplary suitable flavoring agents may include, but not be limited to, "flavor extract" obtained by extracting a part of a raw material, e.g., animal or plant material, often by using a solvent such as ethanol or water; natural essences obtained by extracting essential oils from the blossoms, fruit, roots, etc., or from the whole plants.

Additional exemplary flavoring agents that may be in the dosage form may include, but not be limited to, breath freshening compounds like menthol, spearmint, and cinnamon, coffee beans, other flavors or fragrances such as fruit flavors (e.g., cherry, orange, grape, etc.), especially those used for oral hygiene, as well as actives used in dental and oral cleansing such as quaternary ammonium bases. The effect of flavors may be enhanced using flavor enhancers like tartaric acid, citric acid, vanillin, or the like.

Exemplary sweetening agents may include, but not be limited to, one or more artificial sweeteners, one or more natural sweeteners, or a combination thereof. Artificial sweeteners include, e.g., acesulfame and its various salts such as the potassium salt (available as Sunett®), alitame, aspartame (available as NutraSweet® and Equal®), salt of aspartame-acesulfame (available as Twinsweet®), neohesperidin dihydrochalcone, naringin dihydrochalcone, dihydrochalcone compounds, neotame, sodium cyclamate, saccharin and its various salts such as the sodium salt (available as Sweet'N Low®), stevia, chloro derivatives of sucrose such as sucralose (available as Kaltame® and Splenda®), and mogrosides. Natural sweeteners include, e.g., glucose, dextrose, invert sugar, fructose, sucrose, glycyrrhizin; monoammonium glycyrrhizinate (sold under the trade name MagnaSweet®); Stevia rebaudiana (Stevioside), natural intensive sweeteners, such as Lo Han Kuo, polyols such as sorbitol, mannitol, xylitol, erythritol, and the like.

In some embodiments, the enteric shell composition and/or the enteric softgel capsule may be tested in a disintegration test performed in a basket-rack assembly NT-40H model apparatus in a 1000 mL beaker at about 37° C.±2° C. (described in more detail below). The enteric softgel capsule according to this embodiment may remain intact for about one hour, about two hours, about three hours, about four hours, about five hours, or longer than about 1-5 hours in acidic medium and may disintegrate in about 30 minutes or less in intestinal fluid, in about 20 minutes or less, in about 10 minutes or less, in about 5 minutes or less.

Disintegration tests performed herein are harmonized with the European Pharmacopoeia and the U.S. Pharmacopoeia for enteric coated preparations. The apparatus used for the disintegration tests is of model NT-40H (manufactured by Toyama Sangyo Co. Ltd.). The apparatus being a basket-rack assembly, a 1000-mL, low form beaker, 138 to 160 mm in height and having an inside diameter of 97 to 115 mm for the immersion fluid, a thermostatic arrangement for heating the fluid between 35° C. and 39° C., and a device for raising and lowering the basket in the immersion fluid at a constant frequency rate between 29 and 32 cycles per minute through a distance of not less than 53 mm and not more than 57 mm. The volume of the fluid in the vessel is such that at the highest point of the upward stroke the wire mesh remains at least 15 mm below the surface of the fluid and descends to not less than 25 mm from the bottom of the vessel on the downward stroke. At no time should the top of the basket-rack assembly become submerged. The time required for upward stroke is equal to the time required for the downward stroke, and the change in the stroke direction is a smooth transition, rather than an abrupt reversal of motion. The basket-rack assembly moves vertically along its axis. There is no appreciable horizontal motion or movement of the axis from the vertical. A disk may be added to the apparatus if needed.

The disintegration tests disclosed herein were performed at about 37° C.±2° C. at a volume of fluid of 1000 mL. Disintegration test fluid 1 (also referred to herein as "artificial gastric juice") was 2 g/L sodium chloride-hydrochloric acid solution having a pH of 1.2. Disintegration test fluid 2 (also referred to herein as "artificial intestinal fluid") was 0.2 mol/L potassium dihydrogen phosphate–0.2 mol/L sodium hydroxide solution having a pH of 6.8.

The disintegration test with the first fluid was carried out for about 120 minutes by placing one unit in each of the six tubes of the basket, immersing the basket (and consequently the units) in the first test fluid, and lifting the basket from the fluid to observe whether the units disintegrated. Disintegration is defined as that state at which the unit is broken or the enteric shell composition is ruptured or broken. The test is met if none of the six units is disintegrated. A similar test is performed with the second disintegration test fluid for the selected duration.

In some embodiments, the disintegration test may be performed for about 150 minutes, about 120 minutes, about 105 minutes, about 90 minutes, about 75 minutes, about 60 minutes, about 45 minutes, about 30 minutes, about 15 minutes, about 10 minutes, or about 5 minutes.

Encapsulation of the fill material can be accomplished in any conventional manner. As an example, a rotary die encapsulation may be used.

According to an embodiment, an enteric softgel capsule is prepared by the process comprising the steps of: (a) preparing the fill material, said fill material comprising at least one pharmaceutically active ingredient; and (b) encapsulating the fill material of step (a) in an enteric shell composition. The encapsulation process according to step (b) may further comprise a sub-step of preparing the enteric shell composition by, for example, admixing a gelatin, HPMC, a low methoxy pectin and a plasticizer, wherein the enteric shell composition is free of conventional enteric polymers.

In an embodiment, the enteric shell composition comprises: (a) a gelatin, (b) a cellulose derivative (e.g., "HPMC"), (c) a pectin such as a low methoxy pectin and (d) a plasticizer.

In an embodiment, the enteric shell composition consists essentially of: (a) a gelatin, (b) a cellulose derivative (e.g., "HPMC"), (c) a pectin such as a low methoxy pectin and (d) a plasticizer.

In an embodiment, the enteric shell composition consists of: (a) a gelatin, (b) a cellulose derivative (e.g., "HPMC"), (c) a pectin such as a low methoxy pectin and (d) a plasticizer.

In an embodiment, the enteric shell composition comprises: (a) about 40 wt % to about 80 wt %, about 45 wt % to about 75 wt %, or about 50 wt % to about 70 wt % gelatin, (b) about 0.15 wt % to about 4 wt %, about 0.2 wt % to about 2 wt %, or about 0.25 wt % to about 1.4 wt % of a cellulose derivative (e.g., "HPMC"), (c) about 2 wt % to about 20 wt %, about 3 wt % to about 15 wt %, or about 3 wt % to about 5.5 wt % of a pectin such as a low methoxy pectin and (d) about 15 wt % to about 40 wt %, about 20 wt % to about 35 wt %, or about 25 wt % to about 30 wt % of a plasticizer.

In an embodiment, the enteric shell composition consists essentially of: (a) about 40 wt % to about 80 wt %, about 45 wt % to about 75 wt %, or about 50 wt % to about 70 wt % gelatin, (b) about 0.15 wt % to about 4 wt %, about 0.2 wt % to about 2 wt %, or about 0.25 wt % to about 1.4 wt % of a cellulose derivative (e.g., "HPMC"), (c) about 2 wt % to about 20 wt %, about 3 wt % to about 15 wt %, or about 3 wt % to about 5.5 wt % of a pectin such as a low methoxy pectin and (d) about 15 wt % to about 40 wt %, about 20 wt % to about 35 wt %, or about 25 wt % to about 30 wt % of a plasticizer.

In an embodiment, the enteric shell composition consists of: (a) about 40 wt % to about 80 wt %, about 45 wt % to about 75 wt %, or about 50 wt % to about 70 wt % gelatin, (b) about 0.15 wt % to about 4 wt %, about 0.2 wt % to about 2 wt %, or about 0.25 wt % to about 1.4 wt % of a cellulose derivative (e.g., "HPMC"), (c) about 2 wt % to about 20 wt %, about 3 wt % to about 15 wt %, or about 3 wt % to about 5.5 wt % of a pectin such as a low methoxy pectin and (d) about 15 wt % to about 40 wt %, about 20 wt % to about 35 wt %, or about 25 wt % to about 30 wt % of a plasticizer.

EXAMPLES

Specific embodiments of the invention will now be demonstrated by reference to the following examples. It should be understood that these examples are disclosed solely by way of illustrating the invention and should not be taken in any way to limit the scope of the present invention.

Example 1

Enteric softgel capsules were prepared where the enteric shell had the compositions set forth in Table 1.

TABLE 1

Enteric shell compositions.

| | Formulations | | | | |
|---|---|---|---|---|---|
| | 1<br>% (mg) | 2<br>% (mg) | 3<br>% (mg) | 4<br>% (mg) | 5<br>% (mg) |
| Glycerin | 28.10%<br>(44.19) | 28.10%<br>(44.19) | 28.10%<br>(44.19) | 27.95%<br>(44.19) | 27.82%<br>(44.19) |
| Gelatin | 63.61%<br>(100.00) | 63.60%<br>(100.00) | 63.59%<br>(100.00) | 63.24%<br>(100.00) | 62.95%<br>(100.00) |
| Pectin | 7.95%<br>(12.50) | 7.94%<br>(12.50) | 7.95%<br>(12.50) | 7.90%<br>(12.50) | 7.87%<br>(12.50) |
| HPMC | 0.27%<br>(0.43) | 0.35%<br>(0.55) | 0.38%<br>(0.58) | 0.91%<br>(1.44) | 1.36%<br>(2.16) |
| Total | 157.21 | 157.24 | 157.26 | 158.13 | 158.85 |

Disintegration tests were performed to determine the length of time required for capsule disintegration in artificial gastric fluid and artificial intestinal fluid.

TABLE 2

Results of the disintegration tests.

| Formulations | 1 | 2 | 3 | 4 | 5 |
|---|---|---|---|---|---|
| Gastric fluid | Over 120 min | Over 120 min | Over 120 min | Over 120 min | Over 120 min |

TABLE 2-continued

Results of the disintegration tests.

| Formulations | 1 | 2 | 3 | 4 | 5 |
|---|---|---|---|---|---|
| Intestinal fluid Encapsulation | 5 min pass | 5 min pass | 5 min pass | 5 min pass | 5 min pass |

As seen in Tables 1 and 2, the enteric softgel capsules according to this example did not disintegrate in over 120 minutes in artificial gastric fluid while disintegrating in 5 minutes in intestinal fluid.

Example 2

Enteric softgel capsules with and without HPMC were prepared. The enteric shell compositions are set forth in Table 3.

TABLE 3

Enteric shell compositions with and without HPMC

| Formulations | With HPMC | Without HPMC |
|---|---|---|
| Glycerin | 14% | 16% |
| Gelatin | 32% | 36% |
| Pectin | 4% | 4% |
| HPMC | 0.23% | 0 |

Disintegration tests were performed on the enteric shell compositions of Table 3 to determine the length of time required for capsule disintegration in artificial gastric fluid. The results of the disintegration tests are summarized in Table 4 below.

TABLE 4

Results of the disintegration tests.

| Time/Formulations | With HPMC | Without HPMC |
|---|---|---|
| 20 minutes | No change in film thickness/shape | The film thickness becomes thin |
| 30 minutes | No change in film thickness/shape | The film thickness becomes thinner than observation at 20 minutes |
| 60 minutes | No change in film thickness/shape | The film thickness becomes thinner than observation at 30 minutes |
| 90 minutes | No change in film thickness/shape | The film thickness becomes thinner than observation at 60 minutes. The film remains but is transparent and is not suitable for an enteric shell |

TABLE 4-continued

Results of the disintegration tests.

| Time/Formulations | With HPMC | Without HPMC |
|---|---|---|
| 120 minutes | No change in film thickness/shape | The film thickness becomes thinner than observation at 90 minutes. The film remains but is transparent and is not suitable for an enteric shell |
| 350 minutes | No change in film thickness/shape | — |

Example 3

Enteric shell compositions with varying concentrations of HPMC were prepared to study the effect of the HPMC concentration on the manufacturability of the composition. The enteric shell compositions are set forth in Table 5. "Other Mixture" in Table 5 includes glycerin, gelatin, and pectin.

TABLE 5

Effect of varying amounts of HPMC in the enteric shell composition on manufacturability

| Components | 1 | 2 | 3 | 4 | 5 | 6 | 7 | 8 | 9 |
|---|---|---|---|---|---|---|---|---|---|
| Other Mixture | 50.81 | 50.79 | 50.76 | 50.74 | 50.62 | 50.50 | 50.48 | 51.34 | 50.86 |
| Water | 49.10 | 49.07 | 49.05 | 49.03 | 48.91 | 48.80 | 48.78 | 47.24 | 46.80 |
| HPMC | 0.09 | 0.14 | 0.19 | 0.23 | 0.47 | 0.70 | 0.74 | 1.42 | 2.34 |
| Manufacurability | Less acceptable | acceptable | acceptable | acceptable | acceptable | acceptable | acceptable | acceptable | acceptable |

Example 4

Enteric shell compositions with varying concentrations of pectin were prepared to study the effect of the pectin concentration on the manufacturability of the composition. The enteric shell compositions are set forth in Table 6. "Other Mixture" in Table 6 includes glycerin and gelatin.

TABLE 6

Effect of varying amounts of pectin in the enteric shell composition on manufacturability

| Components | 1 | 2 |
|---|---|---|
| Other Mixture | 51.83 | 48.45 |
| Water | 44.57 | 46.51 |
| Pectin | 3.59 | 5.04 |
| Manufacturability | Acceptable | Acceptable |

What is claimed is:

1. An enteric softgel capsule comprising:
   (a) a fill material; and
   (b) an enteric shell composition,
   wherein the fill material comprises at least one pharmaceutically active ingredient, and
   wherein the shell composition comprises about 40 wt % to about 80 wt % of a gelatin, about 2.0 wt % to about 20 wt % of a pectin, about 0.15 wt % to about 4.0 wt % of a cellulose derivative, and about 15 wt % to about 40 wt % of a plasticizer, wherein the pectin has a degree of esterification lower than about 50%, and wherein the capsule does not include an enteric coating.

2. The enteric softgel capsule of claim 1, wherein the gelatin is selected from the group consisting of type A gelatin, type B gelatin and mixtures thereof.

3. The enteric softgel capsule of claim 1, wherein the gelatin is selected from the group consisting of fish gelatin, hide gelatin, bone gelatin and mixtures thereof.

4. The enteric softgel capsule of claim 1, wherein the plasticizer is selected from the group consisting of glycerol, sorbitol and combinations thereof.

5. The enteric softgel capsule of claim 4, wherein the plasticizer is glycerol.

6. The enteric softgel capsule of claim 1, wherein the cellulose derivative is selected from the group consisting of hydroxypropyl methylcellulose, methyl cellulose, hydroxypropyl cellulose, and combinations thereof.

7. The enteric softgel capsule of claim 6, wherein the cellulose derivative is hydroxypropyl methylcellulose.

8. The enteric softgel capsule of claim 1, wherein the enteric shell composition comprises from about 45 wt % to about 75 wt % of the gelatin.

9. The enteric softgel capsule of claim 8, wherein the enteric shell composition comprises from about 50 wt % to about 70 wt % of the gelatin.

10. The enteric softgel capsule of claim 1, wherein the enteric shell composition comprises from about 3 wt % to about 15 wt % of the pectin.

11. The enteric softgel capsule of claim 10, wherein the enteric shell composition comprises from about 3 wt % to about 5.5 wt % of the pectin.

12. The enteric softgel capsule of claim 1, wherein the enteric shell composition comprises from about 20 wt % to about 35 wt % of the plasticizer.

13. The enteric softgel capsule of claim 12, wherein the enteric shell composition comprises from about 25 wt % to about 30 wt % of the plasticizer.

14. The enteric softgel capsule of claim 1, wherein the enteric shell composition comprises from about 0.20 wt % to about 2.0 wt % of the cellulose derivative.

15. The enteric softgel capsule of claim 14, wherein the enteric shell composition comprises from about 0.25 wt % to about 1.4 wt % of the cellulose derivative.

16. The enteric softgel capsule of claim 1, wherein the capsule disintegrates in less than about 30 minutes in an intestinal environment based on a disintegration test performed in a basket-rack assembly NT-40H model apparatus in a 1000 mL beaker at about 37° C.±2° C.

17. The enteric softgel capsule of claim 1, wherein the capsule disintegrates in about one hour in an acidic medium based on a disintegration test performed in a basket-rack assembly NT-40H model apparatus in a 1000 mL beaker at about 37° C.±2° C.

18. A process of preparing an enteric softgel capsule according to claim 1 comprising the steps of:
   (a) preparing the fill material; and
   (b) encapsulating the fill material with the enteric shell composition.

19. The process according to claim 18 further comprising preparing the enteric shell composition by admixing the gelatin, hydroxypropyl methylcellulose, the pectin and the plasticizer, wherein the enteric shell composition is free of enteric polymers.

* * * * *